United States Patent
Bright et al.

(10) Patent No.: US 7,452,354 B2
(45) Date of Patent: Nov. 18, 2008

(54) IMPLANTABLE PUMP CONNECTOR FOR CATHETER ATTACHMENT

(75) Inventors: Jeffrey D. Bright, Salt Lake City, UT (US); Robert N. Gailey, Farmington, UT (US); Stephen D. Calder, Farmington, UT (US); Paul Burke, Bellingham, MA (US)

(73) Assignee: InSet Technologies Incorporated, Mt. Olive, NJ (US)

( * ) Notice: Subject to any disclaimer, the term of this patent is extended or adjusted under 35 U.S.C. 154(b) by 0 days.

(21) Appl. No.: 10/180,708

(22) Filed: Jun. 26, 2002

(65) Prior Publication Data

US 2004/0002693 A1 Jan. 1, 2004

(51) Int. Cl.
*A61M 25/16* (2006.01)

(52) U.S. Cl. ..................................... 604/533

(58) Field of Classification Search ......... 604/533–539, 604/264, 288.01, 288.04; 285/256
See application file for complete search history.

(56) References Cited

U.S. PATENT DOCUMENTS

| | | | |
|---|---|---|---|
| 2,393,003 A | 1/1946 | Smith | |
| 3,419,010 A | 12/1968 | Williamson | |
| 3,840,009 A | 10/1974 | Michaels et al. | |
| 3,951,147 A | 4/1976 | Tucker et al. | |
| 4,257,421 A | 3/1981 | Beal | |
| 4,310,001 A | 1/1982 | Comben | |
| 4,388,076 A | 6/1983 | Waters | |
| 4,548,607 A | 10/1985 | Harris | |
| 4,559,046 A | 12/1985 | Groshong et al. | |
| 4,583,968 A | 4/1986 | Mahurkar | |
| 4,692,147 A | 9/1987 | Duggan | |
| 4,723,948 A | 2/1988 | Clark et al. | |
| 4,749,217 A | 6/1988 | Causby et al. | ............... 285/245 |
| 4,772,276 A | 9/1988 | Wiita et al. | |
| 4,838,887 A | 6/1989 | Idriss | ....................... 604/891.1 |
| 4,880,414 A | 11/1989 | Whipple | |
| 4,929,236 A | 5/1990 | Sampson | |
| 4,963,133 A | 10/1990 | Whipple | |
| 5,015,238 A | 5/1991 | Solomon et al. | |
| 5,045,064 A | 9/1991 | Idriss | |

(Continued)

FOREIGN PATENT DOCUMENTS

FR 2 750 055 A1 12/1997

(Continued)

OTHER PUBLICATIONS

International Search Report mailed on Oct. 29, 2003, for PCT patent application No. PCT /US 03/20600 filed on Jun. 26, 2003.

*Primary Examiner*—Kevin C. Sirmons
*Assistant Examiner*—Catherine N Witczak
(74) *Attorney, Agent, or Firm*—Nields & Lemack

(57) ABSTRACT

A catheter system for locking a catheter to an implantable pump and for effectively flushing a catheter after implantation within a body. A locking component comprises an extension boot and catheter lock that together fluidly connect the catheter to the pump in a secure, safe and effective manner. A catheter component comprises a design having kink-resistant walls and a unique tip. A flushing component comprises a hub and stylet combination characterized by a hydrophilic coating on the stylet and a flush through hub to allow flushing of the stylet while inside the catheter.

18 Claims, 5 Drawing Sheets

U.S. PATENT DOCUMENTS

| | | | |
|---|---|---|---|
| 5,049,141 A | 9/1991 | Olive | 604/891.1 |
| 5,129,891 A | 7/1992 | Young | |
| 5,167,633 A | 12/1992 | Mann et al. | |
| 5,197,951 A | 3/1993 | Mahurkar | |
| 5,221,255 A | 6/1993 | Mahurkar et al. | |
| 5,295,968 A | 3/1994 | Martel et al. | |
| 5,312,337 A | 5/1994 | Flaherty et al. | |
| 5,328,465 A | 7/1994 | Kratoska et al. | |
| 5,357,961 A | 10/1994 | Fields et al. | |
| 5,395,324 A | 3/1995 | Hinrichs et al. | |
| 5,472,435 A | 12/1995 | Sutton | |
| 5,514,103 A | 5/1996 | Srisathapat et al. | |
| 5,527,307 A | 6/1996 | Srisathapat et al. | |
| 5,575,770 A | 11/1996 | Melsky et al. | |
| 5,632,729 A | 5/1997 | Cai et al. | |
| 5,637,102 A | 6/1997 | Tolkoff et al. | 604/283 |
| 5,700,251 A | 12/1997 | Miyauchi et al. | |
| 5,702,372 A | 12/1997 | Nelson | |
| 5,743,873 A | 4/1998 | Cai et al. | |
| 5,752,930 A | 5/1998 | Rise et al. | |
| 5,769,823 A | 6/1998 | Otto | |
| 5,792,104 A | 8/1998 | Speckman et al. | 604/93 |
| 5,823,961 A | 10/1998 | Fields et al. | |
| 5,833,275 A | 11/1998 | Anderson | |
| 5,833,654 A * | 11/1998 | Powers et al. | 604/93.01 |
| 5,908,414 A | 6/1999 | Otto et al. | |
| 5,925,017 A | 7/1999 | Kriesel et al. | |
| 5,925,030 A | 7/1999 | Gross et al. | |
| 6,003,906 A | 12/1999 | Fogarty et al. | 285/242 |
| 6,039,712 A | 3/2000 | Fogarty et al. | 604/93 |
| 6,045,530 A | 4/2000 | Krueger et al. | |
| 6,050,987 A * | 4/2000 | Rosenbaum | 604/533 |
| 6,083,194 A * | 7/2000 | Lopez | 604/28 |
| 6,086,555 A | 7/2000 | Eliasen et al. | 604/93.01 |
| 6,113,572 A * | 9/2000 | Gailey et al. | 604/93.01 |
| 6,126,650 A | 10/2000 | Martinez et al. | |
| 6,213,973 B1 | 4/2001 | Eliasen et al. | 604/93.01 |
| 6,217,565 B1 | 4/2001 | Cohen | |
| 6,221,064 B1 * | 4/2001 | Nadal | 604/533 |
| 6,231,085 B1 | 5/2001 | Olson | 285/23 |
| 6,234,973 B1 | 5/2001 | Meador et al. | |
| 6,245,029 B1 | 6/2001 | Fujita et al. | |
| 6,287,293 B1 | 9/2001 | Jones et al. | 604/891.1 |
| 6,562,023 B1 | 5/2003 | Marrs et al. | |
| 6,575,959 B1 | 6/2003 | Sarge et al. | 604/533 |
| 6,641,177 B1 | 11/2003 | Pinciaro | 285/242 |

FOREIGN PATENT DOCUMENTS

| | | |
|---|---|---|
| GB | 2 257 764 A | 4/1992 |

\* cited by examiner

IMPLANTABLE PUMP CONNECTOR FOR CATHETER ATTACHMENT

FIELD OF THE INVENTION

The present invention relates to a catheter system and more particularly to a catheter flushing and locking system for use with an implantable pump.

BACKGROUND OF THE INVENTION

Use of implantable pumps for treating chronic pain conditions has become widely accepted practice when more conservative means of relieving pain have failed. Implantable pump technology can be divided into two primary categories, namely constant flow and programmable. Both technologies incorporate an indwelling catheter to establish a fluid path from a pump disposed subcutaneously to a desired anatomical site, including but not limited to, arterial or venous locations, the epidural space and the intrathecal space of the spine. Some of the reported complications with implanted pumps deal with the connection between the pump and the catheter, including leaks, disconnect and reduced flow. Other reported complications involve the catheter itself, which include but are not limited to, kinking, occlusion, disconnect, malposition, migration and reduced flow. Thus, the success of an implanted pump system is dependent in large part on a successful and dependable connection between the pump and the catheter as well as the design of the catheter and the introduction techniques utilized.

Prior art implantable pumps employ relatively tedious and often complicated means for attaching the catheter to the pump, which also may promote problems for the entire pump and catheter system. For example, screw driven clamping connections are both complicated and unreliable as the required clamping action on the outer diameter of an unsupported catheter increases the risk of collapsing the inner lumen of the catheter. Stent based designs that do utilize internal support solve the problem of internal collapse, but require the additional step of attachment involving multiple sutures around the connection area. The suturing process, as well as the sutures themselves, can lead to broken or severed catheters at the suture site where the suture cuts through the catheter or surrounding support members. Also, variability in suture tying and force applied by the user leads to variability in attachment. Thus, a prior art approach to attaching the catheter to the pump has been to utilize a barbed stem connector. The pump is fit with a barbed or flared outer stem for the catheter to be placed therearound. The problem with these designs, which are common in subcutaneous access ports, is a connection that is relatively unsecured and potential damage to the catheter caused by the barbed section. Another related problem is that it is often difficult to ascertain whether a positive connection between the pump and catheter has been established. This can lead to catheter and/or pump damage as undue force is placed on the attachment system in order to get verification of the connection.

In addition to these drawbacks of the prior art systems, one of the primary concerns to overcome in developing a successful and reliable attachment system is that the catheters are generally very small in diameter while the pumps to which they are connected are relatively large. Thus, it is often physically difficult to make the connection between the pump and the catheter.

Accordingly, it is an object of the present invention, in a system involving an implantable pump and catheter, to provide a catheter system for use with implantable pumps and other known catheter-based systems that will maintain the effectiveness and longevity of the connection and system following implantation thereof.

It is also an object of the present invention to provide a connection between the catheter and the pump which eliminates the need for suturing around the catheter, avoids potential collapse of the catheter or other attendant damage thereto.

It is a further object of the present invention to provide a connection system for an implantable pump and catheter that overcomes the difficulty arising from the size difference between the catheter and pump.

It is yet a further object of the present invention to provide a flexible interface between the catheter and pump body to facilitate attachment of the catheter and minimize strains on the connection.

It is still a further object of the present invention to provide a connection system for an implantable pump and catheter, which is very easy and quick to implement.

It is also an object of the present invention to provide a connection system for an implantable pump and catheter that confirms a secure connection.

It is another object of the present invention to provide a connection system for an implantable pump and catheter that is reliable and long-lasting.

It is yet another object of the present invention to provide a catheter with minimal contained dead space at the tip to minimize possible complications from static fluid in the system.

It is still another object of the present invention to provide a stiffening stylet to facilitate positioning of the catheter that is easy to remove and minimizes bunching and displacement of the catheter tip during removal of the stylet.

Further objects and advantages of the present invention will become apparent from the ensuing description and drawings.

BRIEF SUMMARY OF THE INVENTION

In accordance with the present invention, a catheter system for locking a catheter to an implantable pump and for effectively flushing a catheter after implantation within a body is provided. A locking component comprises an extension boot and catheter lock that together fluidly connect the catheter to the pump in a secure, safe and effective manner. A catheter component comprises a design having kink-resistant walls and a unique tip. A flushing component comprises a hub and stylet combination characterized by a hydrophilic coating on the stylet and a flush through hub to allow flushing of the stylet while inside the catheter.

What is claimed is a connection device for attaching a catheter to an implantable port or pump, wherein the catheter is in fluid communication with said port or pump, comprising a coupling device extending from said port or pump, comprising an arm portion and a stem, wherein the shape of the arm portion is substantially similar to an outer contour of said port or pump, and wherein the stem comprises a base portion and a tip portion and a locking device slideable along a length of the catheter, comprising varying diameter portions that communicate directly with diameters of the base portion and tip portion of the stem, wherein a locking connection is established therebetween.

DETAILED DESCRIPTION OF THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

The present invention is directed to a novel attachment device for securely connecting a catheter to a pump, which can be used in a variety of applications to optimize efficiency and effectiveness. The present invention is also directed to a unique catheter configuration, along with means for introduction and positioning thereof within the body, which offers several advantages over prior art catheters and introducing systems and can be used in various applications.

Figure 1:
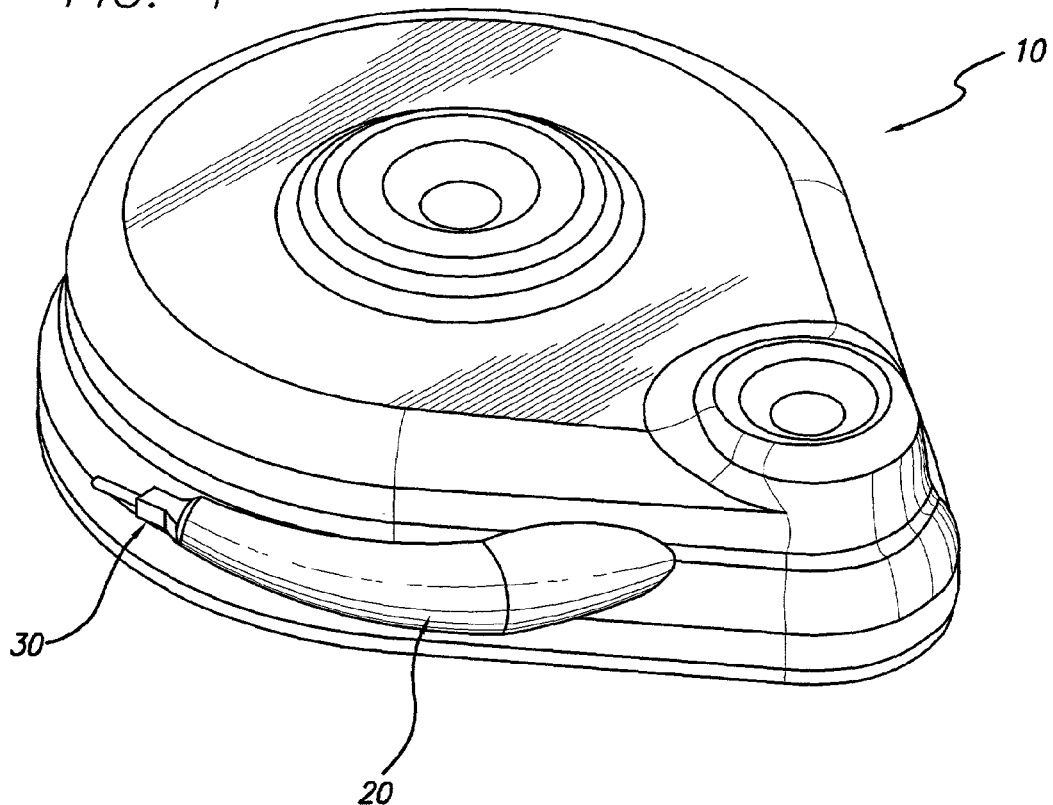
FIG. 1 is a perspective view of an implantable pump with attached boot and stem according to the present invention.

One example of a suitable pump for use with the present invention can be seen in FIG. 1 as implantable pump 10. Implantable pump 10 could be any medical device that is implanted subcutaneously to deliver a steady stream of drugs or other fluids to the body. Generally, the implanted medical device will contain a septum through which an inner chamber to hold and dispense the drug or fluid can be accessed via a needle. The medical device will also have some type of mechanism to release the drug or fluid at predetermined intervals or in a steady stream at a given flow rate. This timed interval or flow rate can be regulated via mechanism within the medical device or outside of the body using other known means.

Examples of implantable medical devices that would be suitable for use in conjunction with the present invention can be found in U.S. application Ser. No. 09/481,298, filed Jan. 11, 2000, entitled "Implantable refillable infusion device and septum replacement kit" and in U.S. Pat. No. 6,287,293, entitled "Method and apparatus for locating the injection point of an implanted medical device;" U.S. Pat. No. 6,213, 973, entitled "Vascular access port with elongated septum;" U.S. Pat. No. 6,086,555, entitled "Dual reservoir vascular access port with two-piece housing and compound septum;" U.S. Pat. No. 5,833,654, entitled "Longitudinally aligned dual reservoir access port;" U.S. Pat. No. 5,049,141, entitled "Programmable valve pump;" and U.S. Pat. No. 4,838,887, entitled "Programmable valve pump," all of which are incorporated by reference herein.

Figure 2:
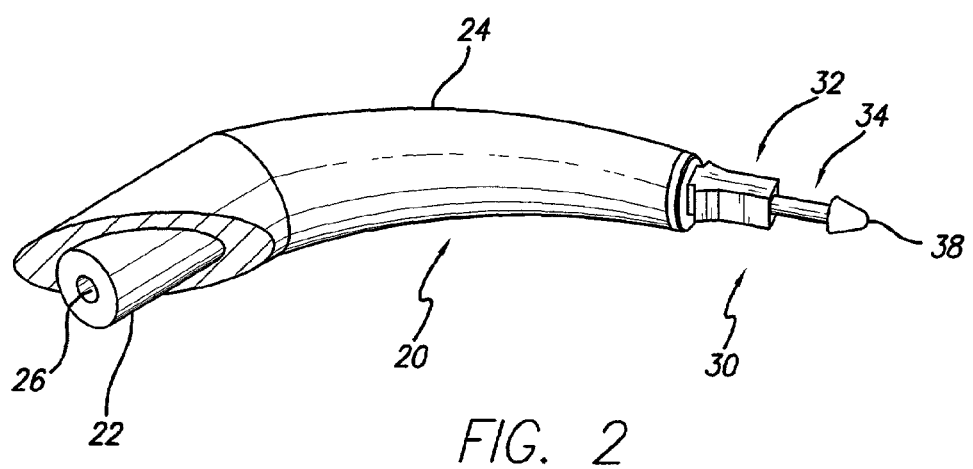
FIG. 2 is a side view of the boot and stem according to the present invention.
Figure 3:
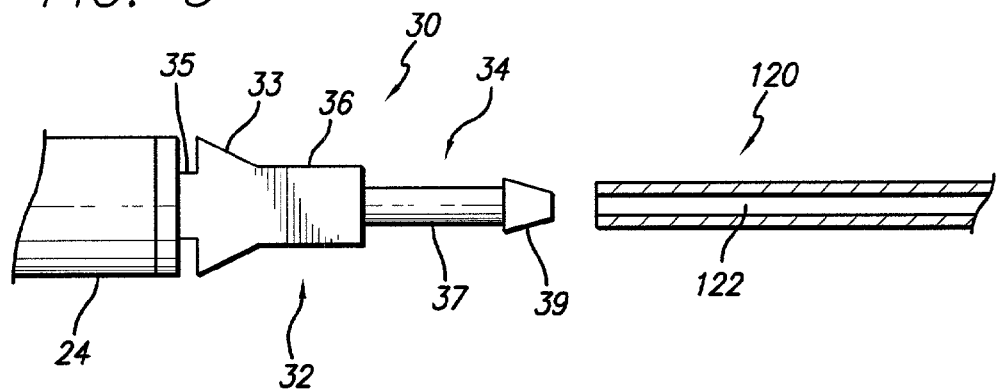
FIG. 3 is an enlarged view of the stem in FIG. 2.

The implantable pump 10 is shown in FIG. 1 with an inventive boot 20 containing a stem 30 according to the present invention, which is shown in more detail in FIGS. 2 and 3. The boot 20 has an arm 24 that is curved to conform to the outside of the pump 10 so that the overall profile thereof is minimized to facilitate implantation and compatibility within the body. While the boot 20 is shown as curved to conform to the shape of the pump 10, in an alternate embodiment a boot would take on any shape of the outer contour of a port or pump to realize the advantages mentioned above. The boot 20 attaches to the implantable pump 10 via connector tube 22, which has a lumen 26 that fluidly connects the inner chambers of the implantable pump 10 (not shown) with the stem outlet 38. Of course, the boot 20 can be adapted further to connect to various shapes and sizes of pumps other than implantable pump 10. For instance, in the case of a conventional port with a straight stem, the boot 20 could be fashioned to replace the straight stem to reduce port profile, or in the case of a dual port system, the boot could likewise be fashioned to accommodate the shape of the housing to reduce the overall space occupied by the port or pump.

Among the many advantages of the conformal shape of the boot are less tissue trauma and reduced force on the catheter and catheter interface with the port or pump (i.e. a stem). Also, in a preferred embodiment of the present invention, the boot is made of a flexible material (such as silicone or a compliant polymer) so that it can be pulled away from the port or pump to which it is attached. This is important because in many applications, the catheters are extremely small, meaning that a physician or medical technician can often find it very difficult to push the catheter onto a stem extending from the port or pump. By providing a flexible boot, the physician or medical technician can pull the boot away from the port or pump, thereby facilitating attachment of the catheter to the stem. After the catheter is sufficiently attached and the boot is released, it will snap back into place, conforming once again to the shape of the port or pump.

In a preferred embodiment of the present invention, the stem 30 contains a base portion 32 and a tip portion 34. As shown in more detail in FIG. 3, the base portion 32 includes a forward portion 36 and an engaging lock portion 33. The engaging lock portion 33 is shown as a larger diameter in a wing configuration near a connecting portion 35 that attaches to the arm 24 of the boot 20. The engaging lock portion 33 is configured to communicate with the geometry of a locking mechanism (see FIG. 4) to secure the catheter 120 to the boot 20. Of course, the engaging lock portion 33 can take on various shapes and sizes and is not confined to the embodiment shown. Indeed, other types of engaging devices could be employed that would certainly be within the scope of the present invention, including twist locks, spring locks, etc.

The tip 34 is configured to receive the catheter 120 such that the lumen 122 of the catheter 120 fits over the tip 34 and is expanded by a tip end 39. Depending on the size of the catheter 120, the size of the tip 34 can vary, but generally, the diameter of a main body 37 of the tip 34 will be slightly larger than the lumen of the catheter so that a tight friction fit between the two is realized. In addition to the friction fit between the main body 37 of the tip 34 and the catheter 120, tip end 39 has a conical shape with a base portion attached to the main body 37 to further ensure a tight fit between the catheter 120 and the tip 34. The diameter of the base portion of the tip end 39 is larger than the diameter of the main body 37 to make disengagement difficult, but not so large that undue stress and resultant damage occurs to the catheter 120 as a result of compression to the wall thereof. The tip end 39 can also take on different forms other than the conical shape shown that will permit the catheter 120 to slide onto the stem 34, while ensuring that sliding off of the stem is unlikely.

Figure 4:
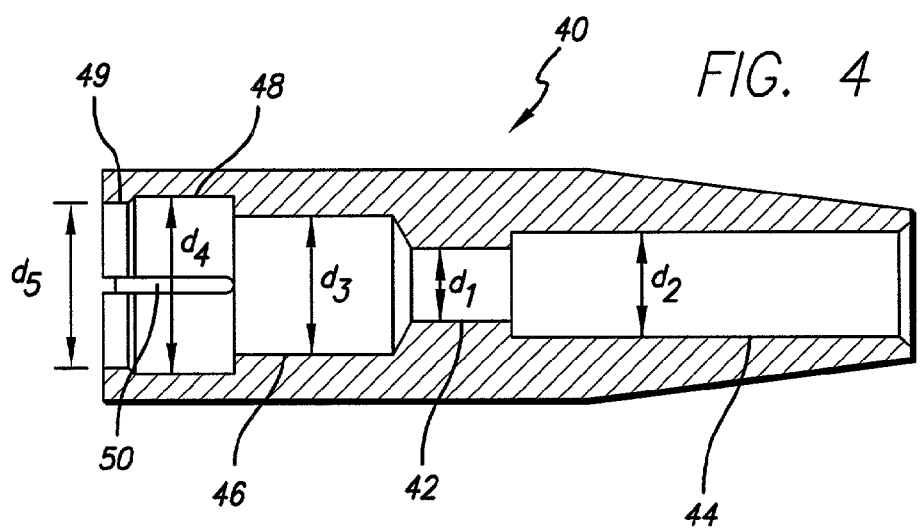
FIG. 4 is a longitudinal cross-sectional view of a catheter lock according to the present invention.
Figure 5:
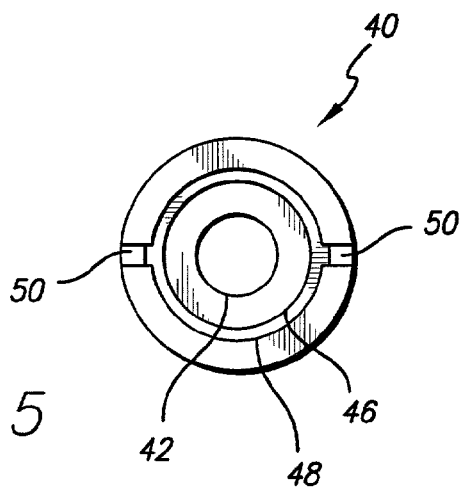
FIG. 5 is an end view of the catheter lock in FIG. 4.
Figure 4A:
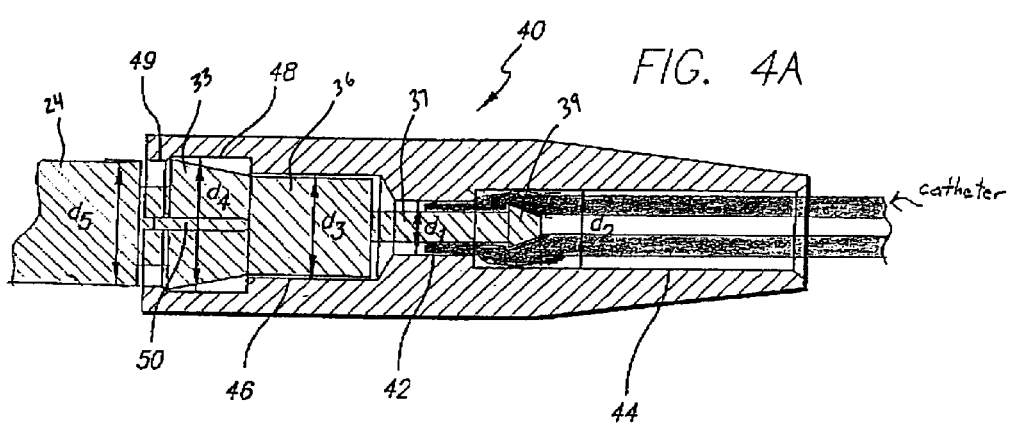
FIG. 4A is a longitudinal crosssectional view of a catheter lock communicating directly with diameters of the base portion of a stem in accordance with the present invention.

Referring now to FIGS. 4 and 5, a catheter lock 40 is shown. FIG. 4 illustrates a longitudinal cross-sectional view of the catheter lock 40, which in the preferred embodiment is made of a hard shell construction (for example, polyacetal resin, polycarbonate or polysulfones) to positively fit over the catheter 120 to secure in place and provide an audible and tactile lock and to provide added security against inadvertent needle sticks. FIG. 5 shows an end view of the catheter lock 40 from the locking end thereof, which is the end that engages with the base portion 32 of the stem 30. Not shown in either view is an optional radiopaque feature, which can be a metal ring, ink or other material on the distal end of the catheter lock 40, providing easy visualization under x-ray or fluoroscopy to verify lock engagement and position. Of course, a radiopaque section could be added to many different portions of the catheter lock 40 for accomplishing the same objective. The catheter lock of the present invention provides an easy, one-step connection mechanism to secure a catheter to an extension of a port or pump, eliminating the need for cumbersome suturing, which may cause damage to the catheter and/or the connection. While a preferred embodiment of the catheter lock is described herein, it should be appreciated that many configurations are possible that would certainly be within the scope of the present invention.

Referring again to FIGS. 4 and 5, the catheter lock 40 has five distinct diameter portions each having a particular function with respect to the locking of the catheter 120 to the stem 30. A middle portion 42 of the catheter lock 40 contains the smallest diameter $d_1$, which is sized slightly larger than the outside diameter of the catheter 120 so that the catheter lock 40 can slide freely along the length thereof. A distal portion 44 of the catheter lock 40 has a slightly larger diameter $d_2$ to allow the catheter 120 to move freely after the catheter lock 40 is secured to the boot 20. The front portion of the catheter lock has three diameter portions 46, 48 and 49, having respective diameters $d_3$ $d_4$ and $d_5$, designed to mate with the base portion 32 of the stem 30, and thereby providing a secondary tactile locking mechanism as will be explained in more detail below. Also positioned in the front portion of the catheter lock 40 are slits 50 positioned on opposite sides thereof to facilitate the movement of the diameter portion 49 of the catheter lock 40 over the engaging portion 33 of the stem 30 and the subsequent locking action therebetween.

The advantage of the catheter boot and locking system as described herein is the ease of connection in combination with the difficult disengagement of the catheter after assembly is complete (will not disengage at clinical loads/extensions). With reference to FIGS. 3 and 4, a catheter connection in a preferred embodiment will be described. After the catheter 120 has been established within the body, for example having an end established in the spine as described above, and is tunneled or otherwise delivered to the location of the pump or port, the catheter connection thereto takes place. As mentioned, the catheter lock 40 is configured to slide freely along the catheter 120 and therefore can be threaded onto the end of the catheter 120 quite easily just prior to connection to the boot 20.

The lumen 122 of the catheter 120 is first slid onto the tip portion 34 of the stem 30 until the catheter 120 is midway along the section 37. The catheter lock 40 is then slid onto the stem 30 and pressed in a direction toward the boot 20 until an audible clicking sound is heard and a positive connection is felt. The slits 50 enable the catheter lock 40 to flex outward slightly when pressed over the engaging portion 33 to facilitate the connection. After connection has been established between the catheter lock 40 and the stem 30, the forward portion 36, having a diameter substantially equal to $d_3$ is within portion 46 and the engaging portion 33, having its largest diameter substantially equal to $d_4$ is within portion 48. Because portion 49 has a diameter $d_5$ slightly smaller than that of the largest diameter of the engaging portion 33, once a connection has been established, the catheter lock cannot be pulled off of the stem 30. Portion 42, having diameter $d_1$, is superimposed over the catheter on section 37 of the stem 30, preventing movement of the catheter within the lock due to the compression applied thereon and providing a primary obstacle for removal of the catheter 120 from the stem 30. In addition, this arrangement acts to seal the connection against fluid leakages between the various interfaces. Portion 49 with diameter $d_5$ provides a secondary obstacle by preventing movement of the catheter lock in a direction away from the boot.

The inventive catheter lock can be used in conjunction with various pumps and ports as mentioned, as well as with a host of different catheters and catheter systems. Examples of intended uses for the catheter system described herein is to deliver pain medicating drug(s) to a patient at locations in the body including the intrathecal space, the epidural space, arterial and venous areas and directly into tissue. A preferred embodiment of the catheter system of the present invention can be seen in FIGS. 6-10.

Figure 6:
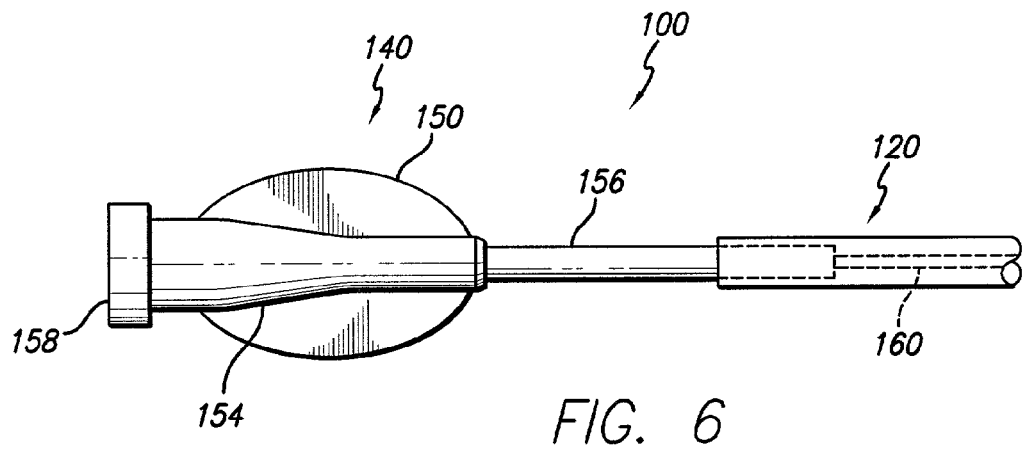
FIG. 6 is a side view of a catheter and flushing hub of the present invention.
Figure 7:
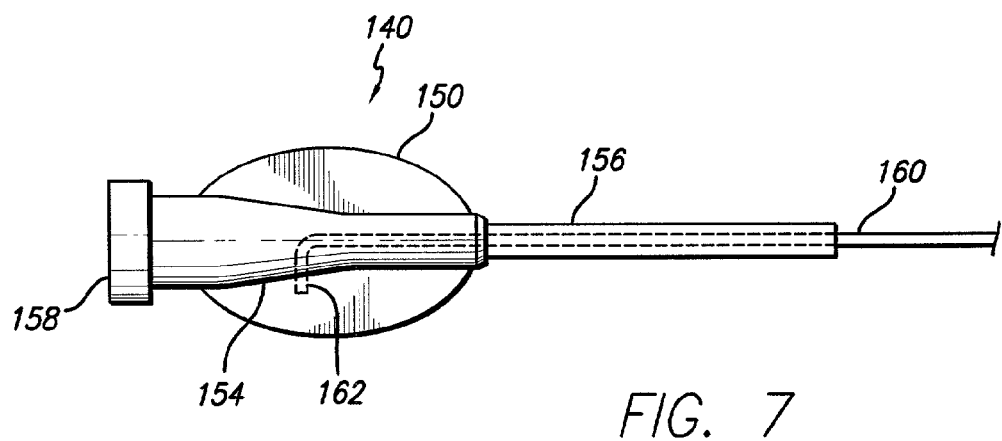
FIG. 7 is a side view of a hub and stylet of the present invention.

Referring to FIG. 6, a catheter system 110 has a flushing hub 140 for flushing a catheter 120 during placement thereof in a patient's body, including a main hub body 154. At a proximal end of the flushing hub 140, an opening 158 provides access to an inner lumen 152 (see FIG. 9). At a distal end of the flushing hub 140, a cannula 156 extends therefrom and is in communication with the inner lumen 152. The cannula 156 surrounds a stylet 160, which can be seen in phantom within the catheter 120, and which is attached to the main hub body 154. The relation between the stylet 160 and the cannula 156 and main hub body 154 can be better seen in FIGS. 7 and 8.

Figure 8:
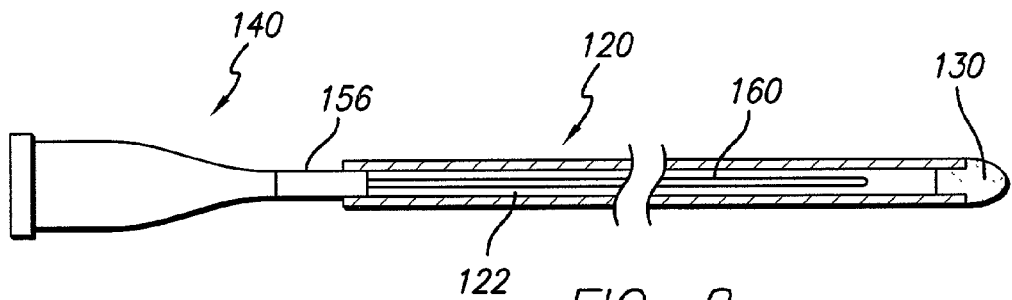
FIG. 8 is perspective view of the hub, stylet and catheter of FIGS. 6 and 7.

FIG. 8 shows the flushing hub 140 and stylet 160 along the length of the catheter 120. The flushing hub 140 allows catheter flushing without removal of the stylet 160 as well as the withdrawal of bodily fluid to confirm catheter location. The stylet 160 provides internal rigidity to the catheter 120 and allows for maneuverability via torque transmission down the stylet 160 from the proximal end of the catheter system 100 to facilitate precise placement of the tip. In the preferred embodiment, the stylet 160 is coated with a hydrophillic coating for ease of removal from the catheter 120. The coating reduces catheter bunching that can compromise the physical properties of the catheter 120 by leading to destructive forces on the catheter 120. The coating further reduces traction internal to the catheter 120 during stylet withdrawal and reduces the potential of tip and/or catheter malposition.

Figure 10:
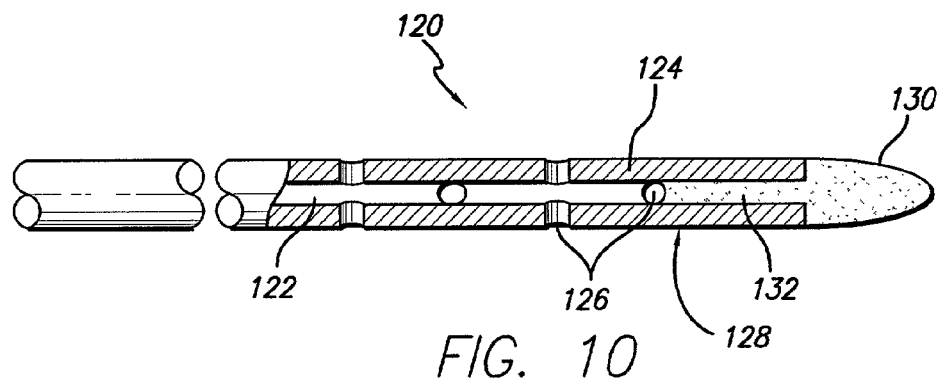
FIG. 10 is a cut away view of a distal end of a catheter of the present invention.

The catheter 120 is closely fitted over the cannula 156 to provide a continuous pathway from the inner lumen 152 of the flushing hub 140 into the lumen 122 of the catheter 120, thereby allowing for the flushing of fluid from the cannula 156 through the lumen of the catheter 120 around the stylet 160 to wet the stylet surface before exiting from the holes 126 at the distal end of the catheter 120 (see FIG. 10).

Figure 9:
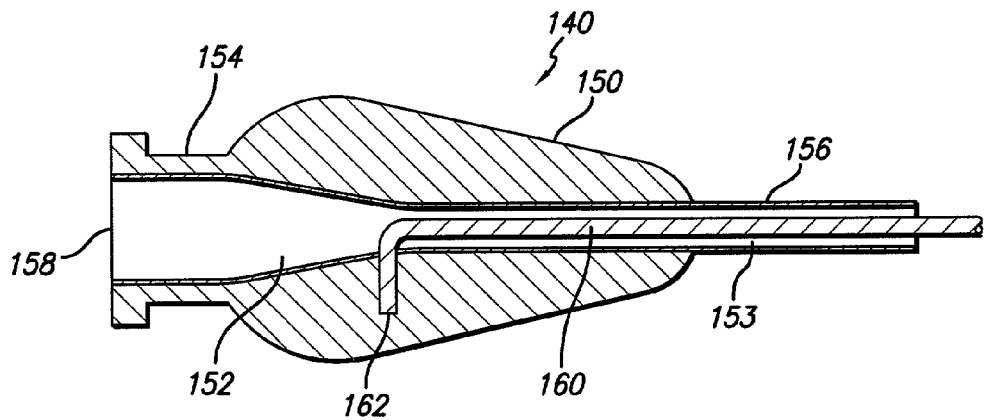
FIG. 9 is a cross-sectional view of the hub and stylet of FIG. 7.

FIG. 9 shows a cross-sectional view of the flushing hub 140. From this view, the inner lumen 152 of the main hub body 154 can be seen, with opening 158 at the proximal end thereof. In this particular embodiment, the stylet 160 is shown affixed to the body 154 and extends through the inner lumen 152, leaving a channel 153 on either side of the stylet 160 for fluid flow. Of course, the stylet 160 could be affixed in other locations not directly within the center of the inner lumen 152 of the main hub body 154. Also, the inner lumen 152 could be differently configured, depending on the features desired in a given catheter system.

Turning now to FIG. 10, a cut-away view of a distal end of the catheter 120 is shown. In the preferred embodiment, catheter 120 has a lumen 122 and walls 124 made of high durometer silicone for kink resistance and its beneficial properties with regard to biocompatibility and biodurability, though other materials are certainly possible that would similarly afford the advantages of the preferred material, such as polyethylene and polyurethane. The walls 124 in the preferred embodiment are relatively thick to further the goal of kink resistance, together comprising approximately half of the external diameter of the catheter (i.e., if the catheter 120 had an outside diameter of nominally 0.055 inches, each wall 124 in cross-section would have a thickness of at least 0.014 inches). At the distal end of the catheter 120, a tip 130 is rounded in the form of a bullet and made of a highly radiopaque material to provide a dual advantage of a geometry that is less traumatic to bodily tissues and anatomical structures and an enhanced visibility, which facilitates location determination during and after introduction to the patient's body. The radiopaque material utilized for the tip 130 in a preferred embodiment is a combination of cured liquid silicone and tungsten powder in approximately 50% by weight of each component.

In the walls 124 of the catheter 120, a set of side holes 126 are provided to allow passage of fluid to and from the lumen 122. The side holes are drilled perpendicular to the surface thereof to limit surface area anomolies that may result in tissue trauma and/or catheter damage upon placement. A catheter segment 128 between the tip 130 and a side hole 126 is filled with similar material as the tip 130 to form plug 132. This feature, combined with the closed-ended geometry of the catheter 120 eliminates dead space that can host proteinaceous material and the like, which, if present within a catheter lumen, can propogate into an occlusion thereof.

As mentioned, one application of the present invention is for use along with an implantable pump to deliver medication to the intrathecal space in a patient's spine. An indwelling catheter, such as catheter 120, is utilized to establish a fluid path from a subcutaneous pump through the dura membrane. The procedure generally consists first of embedding the catheter in the spine (5 to 10 cm). A drop of the spinal fluid is then allowed to form at the proximal end of the catheter 120 to confirm catheter location, after which the catheter is clamped. A tunnel is formed from the spine to the area of the abdomen, where the pump will be implanted, and the catheter is pulled through and cut to length. The catheter is then attached to the pump as described above through the use of an inventive boot and catheter lock. The pump is placed in a previously created pocket in the area of the abdomen and the pocket is closed. Implantation of the described system is relatively quick and easy and provides for prolonged delivery of drugs or medication to the spine.

The present invention has been described above in terms of a presently preferred embodiment so that an understanding of the present invention can be conveyed. However, there are many alternative arrangements for a catheter system not specifically described herein but with which the present invention is applicable. For example, there are many different applications and configurations for a catheter locking system that would be within the scope of the present invention and similarly, there are many applications for a catheter and flushing system other than those specifically described. Although specific features have been given, the catheter system for locking a catheter to an implantable pump and for effectively flushing a catheter after implantation within a body of the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

We claim:

1. A connection device for attaching a catheter to an implantable port or pump, wherein the catheter is in fluid communication with said port or pump, comprising: a coupling device for extending from said port or pump, comprising an arm portion and a stem, wherein the shape of the arm portion is substantially similar to an outer contour of said port or pump, and wherein the stem comprises a base portion and a tip portion, said base portion having a forward portion having a forward portion diameter and an engaging locking portion having varying engaging locking portion diameters including a largest engaging locking portion diameter that is larger than said forward portion diameter, said stem further comprising a connecting portion connecting said base portion to said arm, said connecting portion having a diameter smaller than said largest engaging locking portion diameter, said tip portion having a tip portion diameter; and a locking device slideable along a length of the catheter, comprising varying diameter portions that communicate directly with diameters of the base portion of the stem, said locking device including a first diameter portion larger than said tip portion diameter, a second diameter portion for mating with said forward portion, a third diameter portion substantially equal to said largest engaging locking portion diameter, and a fourth diameter portion smaller than said largest engaging locking portion diameter, whereby when said catheter is inserted onto said tip portion and said locking device is slid onto said stem, a primary locking connection and fluid seal are created in said first diameter portion between said tip portion and said catheter, a secondary locking connection is established in said third diameter portion, and said connecting portion is positioned in said fourth diameter portion, wherein said primary and secondary locking connection are achieved without requiring rotation of said locking device relative to said stem, and whereby lateral movement of said catheter is prevented.

2. The connection device according to claim 1, wherein the diameter of the forward portion is constant.

3. The connection device according to claim 1, wherein the diameter of the engaging portion tapers down to the diameter of the forward portion.

4. The connection device according to claim 1, wherein the tip portion of the stem comprises a barbed end, having a diameter larger than a lumen of the catheter.

5. The connection device according to claim 1, wherein an audible confirmation is provided upon establishment of said locking connection.

6. The connection device according to claim 1, wherein a tactile confirmation is provided upon establishment of said locking connection.

7. The connection device according to claim 1, wherein the arm portion is comprised of a flexible material and is biased to a resting position in close proximity to said port or pump, wherein said arm portion is movable to a connecting position away from said port or pump, and wherein said arm portion retracts to said resting position upon release from said connecting position.

8. The connection device according to claim 1, wherein the stem is comprised of titanium.

9. The connection device according to claim 1, wherein the stem is comprised of stainless steel.

10. The connection device according to claim 1, wherein the locking device is comprised of plastic.

11. The connection device according to claim 1, wherein the locking device comprises a radiopaque portion.

12. The connection device according to claim 11, wherein the radiopaque portion comprises a metal ring.

13. The connection device according to claim 11, wherein the radiopaque portion comprises radiopaque ink.

14. The connection device according to claim 1, wherein said first diameter portion of the locking device is adjacent the second diameter portion of said locking device.

15. The connection device according to claim 14, wherein said third diameter portion is adjacent the second diameter portion of said locking device.

16. The connection device according to claim 15, wherein said fourth diameter portion is adjacent the third diameter portion of said locking device.

17. The connection device according to claim 16, wherein adjacent the diameter of said fourth diameter portion is less than the diameter of the third diameter portion.

18. The connection device of claim 1, wherein said fourth diameter portion is defined by a wall having slits formed therein to facilitate movement of said wall over said portion of said stem having said largest engaging locking portion diameter.

* * * * *